United States Patent [19]
Lieberman et al.

[11] Patent Number: 6,149,609
[45] Date of Patent: Nov. 21, 2000

[54] METHOD AND APPARATUS FOR IMPROVING VISION

[75] Inventors: David Lieberman, New York, N.Y.; Jonathan Grierson, Atwater, Ohio

[73] Assignee: Scientific Optics, Inc., New York, N.Y.

[21] Appl. No.: 09/063,108

[22] Filed: Apr. 20, 1998

Related U.S. Application Data

[62] Division of application No. 08/731,344, Oct. 11, 1996, Pat. No. 5,807,381.
[60] Provisional application No. 60/005,571, Oct. 18, 1995.

[51] Int. Cl.[7] .............................. A61B 17/32; A61N 5/06
[52] U.S. Cl. .............................. 600/587; 606/5; 606/166
[58] Field of Search ........................ 606/5, 166; 600/587; 348/78

[56] References Cited

U.S. PATENT DOCUMENTS 4,669,466 6/1987 L'Esperance .

*Primary Examiner*—Michael H. Thaler
*Attorney, Agent, or Firm*—Darby & Darby

[57] ABSTRACT

Methods and apparatus are disclosed for causing the optical center of the eye to align "HIGH point" of the anterior surface of the cornea. In accordance with one aspect of the invention relating to corneal ablation procedures, the HIGH point of the eye is used as the pole of a spherical surface which is fitted approximately to a portion of the anterior surface of the cornea within a "bounded region." For corneal ablation procedures, the "bounded region" comprises a generally inverted-cup shaped region of the anterior surface of the eye bounded at its periphery by a plane which is substantially perpendicular to a local z-axis. During the operation local high points which project above the spherical surface are ablated. According to another aspect of the invention relating to radial keratotomy procedures, a pair of incisions in the plane of a "great circle" are formed in the cornea to weaken and flatten it. As used herein, a "great circle" is formed by a plane containing the HIGH point and parallel to the local z-axis. The "bounded region" for radial keratotomy procedures is defined absolutely in terms of a circle projected onto the corneal surface which is centered about an axis passing through the HIGH point and parallel to the z-axis.

18 Claims, 8 Drawing Sheets

METHOD AND APPARATUS FOR IMPROVING VISION

This is a division of application Ser. No. 8/731,344, filed Oct. 11, 1996, now U.S. Pat. No. 5,807,381 and claims benefit to U.S. Provisional Applicaton No. 60/005,571 filed Oct. 18, 1995. Each of these prior applications is hereby incorporated herein by reference, in its entirety.

FIELD OF THE INVENTION

The present invention relates to a method and apparatus for improving the vision of an eye.

BACKGROUND OF THE INVENTION

Most common defects in human vision are caused by the shape of the cornea of the eye. For example, nearsightedness can be attributed to a cornea in which the surface curvature is too small, farsightedness can be attributed to a cornea in which the surface curvature is excessive, and astigmatism can attributed to a cornea with irregular surface curvature. Ophthalmologists model the cornea as a portion of an ellipsoid defined by orthogonal major and minor axes. Surgical procedures for correcting visual acuity are typically directed at increasing or decreasing the surface curvature of the cornea, or making its shape more spherical.

In conjunction with modern corneal procedures, such as radial keratotomy and corneal ablation surgery, and for clinical applications, high resolution cameras are used to obtain a digitized array of discrete data points on the corneal surface. One system and camera useful for mapping the cornea is the PAR Corneal Topography System (PAR CTS) available from PAR Vision Systems. The PAR CTS maps the corneal surface topology in two-dimensional Cartesian space, i.e., along x- and y-coordinates, and locates the "line-of-sight", which is then used by the practitioner to plan the surgical procedure. The "line-of-sight" is a straight line segment from a fixation point to the center of the entrance pupil. As described more fully in Mandell, *"Locating the Corneal Sighting Center From Videokeratography,"* J. Refractive Surgery, V. 11, pp. 253–259 (July/August 1995), a light ray which is directed toward a point on the entrance pupil from a point of fixation will be refracted by the cornea and aqueous and pass through a corresponding point on the real pupil to eventually reach the retina.

The point on the cornea at which the line-of-sight intersects the corneal surface is the "optical center" or "sighting center" of the cornea. It is the primary reference point for refractive surgery in that it usually represents the center of the area to be ablated in photorefractive keratectomy and the center of the area to be spared in radial keratotomy. The line-of-sight has conventionally been programmed into a laser control system to govern corneal ablation surgery and as a reference line about which a radial keratotomy procedure is performed. However, some surgeons prefer to use the pupillary axis as a reference line. Experienced practitioners have employed various techniques for locating the sighting center. In one technique, the angle lambda is used to calculate the position of the sighting center relative to the pupillary ("optic") axis. See Mandell, supra, which includes a detailed discussion of the angles kappa and lambda, the disclosure of which is incorporated herein by reference as if set forth in its entirety herein.

In corneal ablation procedures, a portion of the corneal surface is ablated. The gathered elevational data is used to direct an ablation device such as a laser so that the corneal surface can be selectively ablated to more closely approximate a spherical surface of appropriate radius about the line-of-sight, within the ablation zone. In radial keratotomy ("RK") procedures, a series of radially directed, circumferentially spaced incisions are made on the corneal surface about the line-of-sight to weaken the corneal walls and permit the cornea to sit flatter, that is, to have a larger radius of curvature.

In ablation and RK procedures, the use of the line-of-sight as a reference line for the procedures may reduce myopia or otherwise correct a pre-surgical dysfunction. However, a more irregularly shaped cornea may result, which may exacerbate existing astigmatism or introduce astigmatism in the treated eye.

For example, an RK procedure that is performed with respect to the line-of-sight typically reduces myopia, but the incisions, which are made of equal length when viewed in two-dimensional projection, are actually of unequal length along the surface of the cornea, unless the cornea has a symmetrical topology. The RK procedure will therefore introduce an undesirable asymmetry in the cornea, resulting in irregular astigmatism. This will complicate any subsequent vision correction measures that need be taken. Also, any substantial surface irregularities which are produced can cause development of scar tissue or the local accumulation of tear deposits, either of which can adversely affect vision.

Implicit in the use of the-line-of sight or the pupillary axis as a reference axis for surgical procedures is the assumption that the cornea is symmetric about an axis extending along a radius of the eye. However, clinical measurements performed with the PAR CTS, as analyzed in accordance with the method of the present invention, reveal that the cornea exhibits a tilt, typically a forward and downward tilt, relative to the eye. This tilt may be as great as 6° and, on the average, is between 2° and 3°. Hence, a corneal ablation procedure which utilizes the line-of-sight or pupillary axis as a reference axis tends to over-ablate some portions of the cornea and under-ablate other portions of the cornea. At the same time, it changes the geometric relationship between the cornea and the remainder of the eye. Thus, any ablation procedure which does not take into account the tilt of the cornea is not likely to achieve the desired shaping of the cornea and may therefore be unpredictable in its effect.

Analysis of clinical measurements in accordance with the method of the present invention also reveals that that point on the surface of the cornea which is most distant from the reference plane of the PAR CTS (hereafter referred to as the HIGH point) is a far more effective reference point for corneal ablation than the center of the cornea. Specifically, as demonstrated below, laser ablation about an axis passing through the HIGH point produces a much more regularly shaped cornea and removes substantially less corneal material than the same operation performed about an axis close to the center of the eye, such as the pupillary axis.

Recently, the use of a collagen gel has been proposed as a vehicle to facilitate smoothing of the corneal undulations. See Ophthalmology Times, *"Slick Start, Clear Finish,"* 1995, pp. 1 and 24 (Jun. 19–25, 1995) and Review of Ophthalmology, *"News & Trends: Researchers Unveil New Ablatable Mask,"* pp. 12–13 (June 1995), the disclosures of which are incorporated herein by reference as if set forth in their entirety herein. A Type 1 collagen is molded between a contact lens and the anterior surface of the cornea to form a gel mask. The surgeon can adjust the curvature of the postoperative cornea by selecting a flatter or steeper lens, as desired. Reportedly, the gel mask does not shift when hit by laser pulses. Therefore, instead of selective ablation of predetermined locations of the cornea, the masked cornea can be ablated to a uniform depth, thereby conforming the surface contour of the cornea to the lens. A smooth postoperative cornea results, and refractive power correction can be achieved. However, because the ablation operation is centered on the optical center of the cornea or the center of the pupil and does not allow for corneal tilt, the postoperative eye may exhibit an irregular shape or more corneal material may be removed than is necessary.

What is needed in the art and has heretofore not been provided is a method of correcting vision that avoids one or more of these problems, that can produce predictable results, and that provides corrected vision with respect to the particular topology of the patient's eye on which the correction is being performed.

It is therefore one object of the present invention to provide a method for improving the vision of an eye.

It is an additional object of the present invention to provide an improved surgical method for a corneal ablation procedure.

It is a further object of the invention to provide an improved surgical method for an RK procedure.

It is also an object of the present invention to provide a method and apparatus for diagnosing and analyzing a presurgical eye for the purpose of predicting the post-operative condition of the eye and planning more effective surgery.

In accordance with the invention, these objects are achieved by causing the optical center of the eye to align with the "HIGH point" of the cornea.

In accordance with the present invention, these objects are achieved, in part, by performing corneal ablation and RK procedures of the eye in a manner which does not interfere with the natural tilt of the cornea relative to the remainder of the eye.

According to one aspect of the invention relating to corneal ablation procedures, the HIGH point of the cornea is used as the pole of a spherical surface which is fitted approximately to a portion of the anterior surface of the cornea within a "bounded region." For corneal ablation procedures, the "bounded region" comprises a generally inverted-cup shaped region of the anterior surface of the eye bounded at its periphery by a plane which is substantially perpendicular to the z-axis of the bounded region. During the operation local high points which project above the spherical surface are ablated.

According to another aspect of the invention, ablation surgery of the eye is performed by first depositing a setable collagen gel on the cornea, placing a lens on the collagen so that the center of the lens aligns with the HIGH point of the cornea, molds the collagen between the lens and cornea, and permits the collagen gel to set whereby the anterior surface is formed into a spherical mask which is centered over the HIGH point. The mask is then ablated to a uniform depth.

According to another aspect of the invention relating to radial keratotomy procedures, a pair of incisions in the plane of a "great circle" are formed in the cornea to weaken and flatten it. As used herein, a "great circle" is formed by a plane containing the HIGH point and parallel to the z-axis of the bounded region. The "bounded region" for radial keratotomy procedures is defined absolutely in terms of a circle projected onto the corneal surface which is centered about an axis passing through the HIGH point and parallel to the z-axis of the bounded region.

According to a further aspect of the invention, an apparatus for performing radial keratotomy on an eye is disclosed. The apparatus preferably includes a housing adapted to be selectively attached to the cornea by a vacuum so that the housing remains in a fixed position with respect to the cornea during radial keratotomy. A first means associated with the housing is provides a first, regular shape on the cornea which is circular in two-space. A second means associated with the housing provides a second, irregular shape on the cornea. The first and second shapes are disposed on the anterior surface of the cornea such that one surrounds the other. The apparatus is further includes a radially movable blade mounted so that radial movement of the blade in the plane of the great circle from one of the first and second shapes to the other on either side of the HIGH point of the cornea results in incisions in the cornea.

According to yet another aspect of the invention, vision correction is achieved without surgery. Use is made of a contact lens of a type which assumes a predetermined position and orientation when placed in a patient's eye, and the lens is constructed so that its optical center is aligned with the HIGH point of the cornea when the lens is inserted into the patient's eye. Thus when the lens is worn, the optical center of the eye and HIGH point of the cornea are aligned.

These and other objects, features and advantages of the present invention will be readily apparent from the following detailed description taken in conjunction with the accompanying unscaled drawings.

DESCRIPTION OF THE DRAWINGS

FIG. 10, comprising FIG. 11, comprising

DETAILED DESCRIPTION OF THE INVENTION

Figure 1:
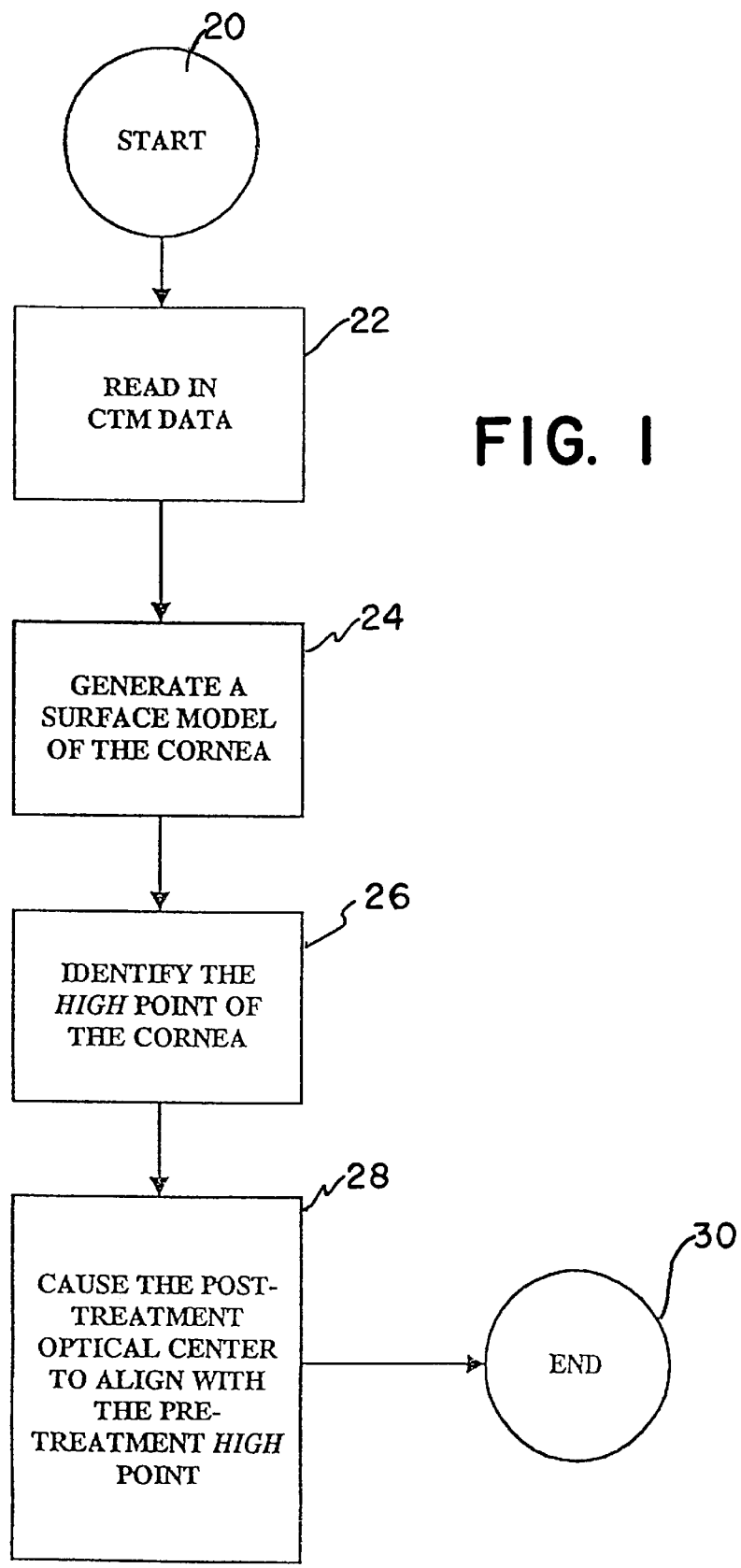
FIG. 1 is an overall flow chart for the method of the invention.

By way of overview and introduction, a method is described according to which procedures are performed to bring the optical center of the eye into alignment with the HIGH point of the cornea, without changing the geometric relationship (tilt) between the cornea and the eye. In the flow chart of FIG. 1, the overall method starts at step 20 with a patient having an improperly shaped, aspherical and/or asymmetric cornea for which surgical correction is appropriate. At step 22, information from a corneal topographic scanning machine in the form of a corneal topographic map ("CTM") is read into a digital computer having a central processor and a computer-readable memory communicatively associated therewith. The CTM data is conventionally available as a data file in either DXF (Data Exchange File) or ASCII formats. The CTM data is obtained with the patient's eye and the corneal topographic scanning machine in fixed relationship to each other so that the coordinate data can be used in a treatment procedure (as at step 28). For example, the surgical tool used for a radial keratotomy or ablation procedure is preferably provided with a suction mount so that the cornea and surgical tool are selectively attached.

The data is arranged as an array of x-, y-, z-coordinates, also known as an array of ordered triples, which generally describes the point-by-point behavior of the mapped corneal surface. Typically, the x and y coordinates are measured in a predefined plane perpendicular to the pupillary axis and the z coordinate is measured along the pupillary axis. The set of all data provided in the CTM, or a set formed from that data, comprises the working universe, or point cloud, from which subsets of ordered triples may be selected and utilized by the computer to generate a surface model of the cornea in accordance with the present invention, as at step 24. The HIGH point of the patient's cornea is identified at step 26 from the CTM data. According to the invention, a procedure causes the post-treatment optical center of the patient's eye to align with the HIGH point of the cornea at step 28. Preferably, the procedure is performed at the same time that the CTM data is acquired so that an absolute coordinate system is established between the corneal topographic machine and the eye. The method of the invention ends at step 30, with the patient having a properly shaped, highly spherical and symmetric post-treatment cornea.

In conventional corneal ablation procedures, the undulations and irregularities in a four to six mm bounded region surrounding a reference axis, (the line-of-sight or pupillary axis) are ablated using, for example, a laser. While with existing procedures the post-surgical cornea may be made to have a smooth and relatively flat surface about the reference axis, irregularities tend to occur closer to the edges of the bounded region, where the ablated portion of the cornea merges with the non-ablated. These types of irregularities can be reduced somewhat by introducing a transition region between the ablated region and the non-ablated region, at the expense of reducing the size of the spherical region of the cornea.

Conventional ablation procedures do not account for the tilt of the cornea and, therefore, tend to over-ablate some areas while under-ablating others, leading again to unnecessary surface irregularities. Such irregularities can be avoided by ablating about a "z-axis" the axis which passes through the HIGH point and is perpendicular to the base plain of the bounded region.

Figure 2:
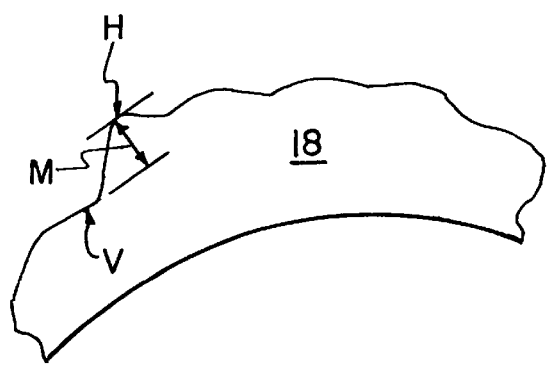
FIG. 2 is an expanded cross-sectional view of a cornea of an eye illustrating typical undulations therein.

The cornea 18 is about 600 $\mu$m thick. In most corneal ablation procedures, less than 100 $\mu$m depth of cornea is ablated because there is virtually no risk of scarring with the type of lasers that are typically used. Beyond the 100 $\mu$m depth, the risk of scarring increases. For example, 120 $\mu$m depth ablation is known to cause scarring; however, there exists the possibility that the risk of scarring for deeper ablations may be reduced by drug therapy prior to or contemporaneous with the laser treatment. The magnitude, M, of the corneal undulations (as shown diagrammatically in FIG. 2) is typically about fifteen to twenty microns from the crest of a hill, H, to the trough of a valley, V, and may be as great as about thirty microns.

The proposed use of a collagen gel, for example, A Type 1 collagen, to mold a smooth spherical surface on the cornea using a temporary mask allows the cornea to be ablated uniformly to the spherical shape defined by the mask. However, because conventional lenses do not seat themselves predictably about a particular point on the eye, the ablation procedure relying on them will result in not maintaining corneal tilt, because the art has not recognized the need to orient the lens so as to retain corneal tilt or to locate the optical center of the eye at the HIGH point of the cornea.

Figure 6:
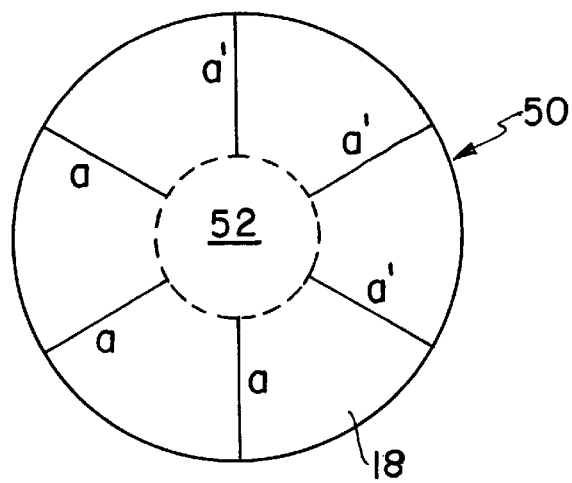
FIG. 6 is a schematic top-elevational view of a radial keratotomy procedure according to known methods.
Figure 7:
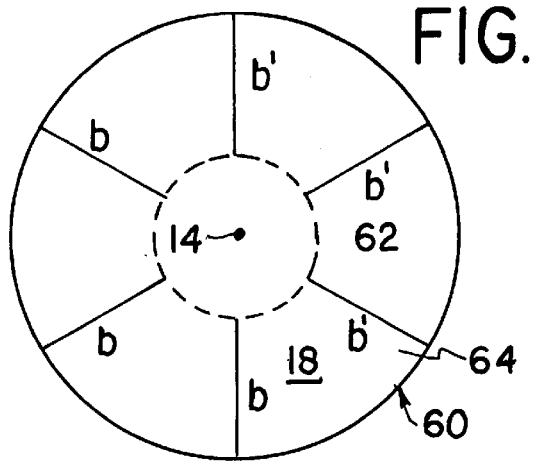
FIG. 7 is a schematic top view of a radial keratotomy procedure according to the invention.

With regard to conventional RK procedures, a marker is used to delineate at least a circle 50, in two-space projection, on the surface of the cornea using temporary ink, as illustrated in FIG. 6. The marker may also delineate guide lines for the radial cuts on the corneal surface (not shown). A diamond knife is then placed over the cornea and the blade is moved radially a fixed distance to slice the cornea 18 at opposed locations a, a' on either side a central portion 52. (The central portion 52 remains uncut to preclude scarring and minimize distortion in the optics in this region of the cornea.) However, because the topology of the typical cornea is not symmetric, the actual length of the opposing radial slices a, a' along the surface of the cornea will differ on either side of the central portion 52, and the post-surgical cornea 18' will likely exhibit asymmetry about the central portion 52. For example, it has been observed in one patient's eye that slices on either side of a central region 52 using a 9 mm outer marker and a 4 mm inner marker, which slices were intended to be 2.5 mm in length, resulted in one of the slices being 2.6684 mm along the corneal surface and the other being 2.9619 mm. The 293 micron variation between these two slices resulted in a cornea that exhibited an undesired and unaccounted for asymmetry. To an extent, this variation in slice lengths is observable in all non-symmetric corneas, the foregoing being illustrative of but one case study.

Illustrative procedures performed at step 28 are described next, followed by a demonstration of the clinical use of the modelling techniques of the invention and a discussion of the creation of a surface model of the cornea.

Selective Corneal Ablation

Figure 3:
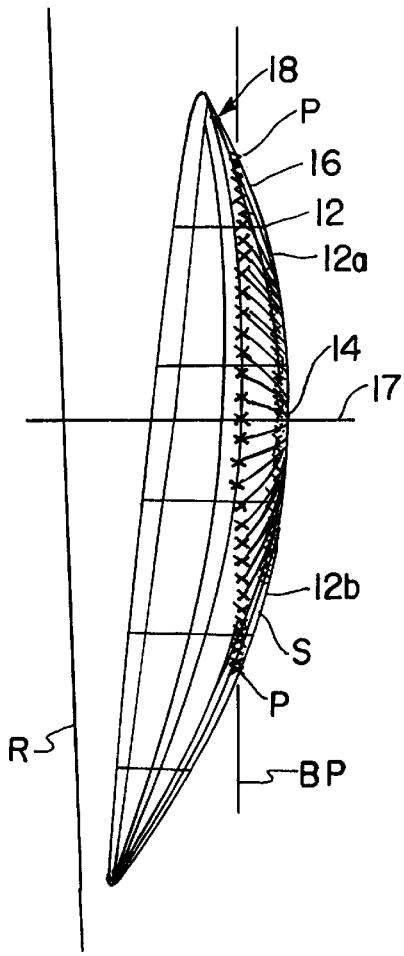
FIG. 3 is a side view of the cornea of an eye as modeled in accordance with the present invention.

FIG. 3 illustrates the cornea 18 as modeled in accordance with the present invention, as described below. The cornea is shown in relationship to the reference plane, R, of the corneal topography scanning machine. As shown, the bounded region 16 on the surface of the cornea is modelled by a plurality of splines, all of which pass through the HIGH point 14 of the cornea and are rotationally spaced at regular intervals, preferably every 5 degrees. Each spline, S, contacts the peripheral margin P of the bounded region 16 at either end. In this example the cornea is tilted relative to the reference plane R, and the periphery, P, of the bounded region 16 is also tilted relative to the reference plane R but at a different angle than the overall cornea (this is a local tilt angle). Since the periphery P is oval, it lies in a plane, hereafter referred to as the base plane (BP).

Figure 4:
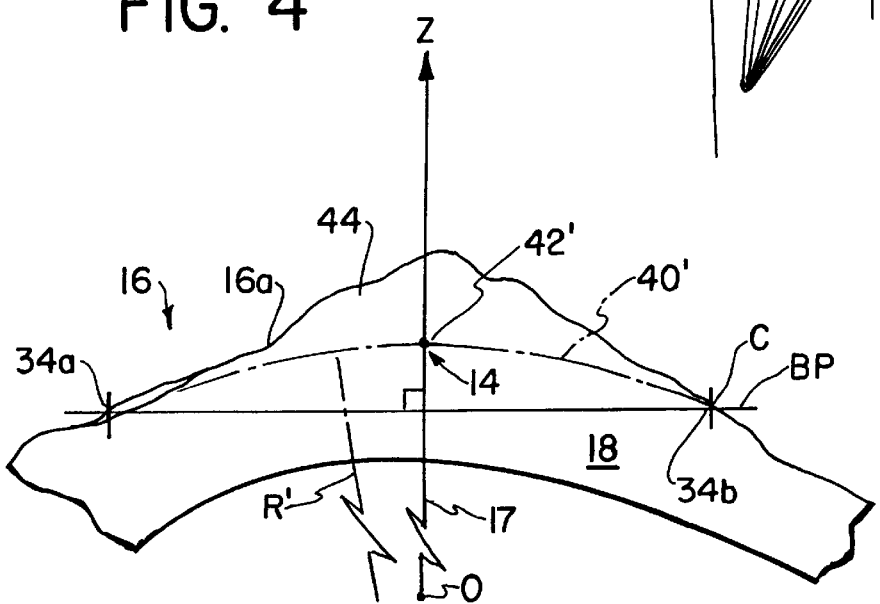
FIG. 4 is an schematic side view of the cornea of an eye having an asymmetric surface, illustrated as it would appear if projected into two-dimensions.

According to the present method and as illustrated in FIG. 4, a bounded region 16 is selected which defines the anterior surface portion 16a of the cornea 18 which is to be fit to a spherical surface by selectively ablating corneal material. The anterior surface portion 16a is the only portion that will be reshaped by the ablation procedure, and a suitable bounded region 16 is selected on a patient-by-patient basis by the surgeon or by a programmed computer, for example, by comparing the patient's cornea (or the surface model) with information known by the surgeon (or information stored in a knowledge base of a digital computer's memory), as understood by those skilled in the art. The bounded region may, for example, be defined by the intersection with the cornea of a base plane BP to produce an anterior surface portion 16a, above the base plane, which extends in three-dimensional space about four to six mm between opposed points 34a and 34b on the boundary. One way of generating the boundary of the bounded region 16 and the base plane is to project a circle C of appropriate diameter on the cornea along an axis which passes through the HIGH point and is parallel to the z axis of the corneal topography scanning machine, typically the pupillary axis. It will be appreciated that this is equivalent to determining the intersection with the corneal surface of a cylinder of diameter C which has an axis that passes through the HIGH point and is parallel to the pupillary axis. In selecting the bounded region 16, the surgeon would consult topological data, in an effort to avoid a region which contains scars or insufficient topological data.

The projected circle C will define an ellipse on the surface of the cornea, and the plane of that ellipse is the BP. The corneal z axis 17 may then be constructed as a line which passes through the HIGH point and is perpendicular to the plane of the ellipse (BP).

In order to perform the ablation, an imaginary sphere 40, is first constructed on the model, which represents the pre-operative status of the spherical region that is to be created. This sphere 40 has its center O on the corneal z-axis 17, and the radius R of the sphere is selected to be the smallest radius such that all points on the surface of the cornea are contained within a region of sphere 40 no greater than a hemisphere. R is considered the pre-operative radius of curvature. The required change in the radius R to produce the post-operative radius of curvature R' is determined in order to achieve a certain visual correction in the post-operative eye. This is a computation that is well-known to those skilled in the art. It is then only necessary to position the center 0 of a sphere 40' with a radius R' so that all points on the surface of the cornea lie on or above sphere 40'. As can be seen in FIG. 4, when the radius of curvature of the cornea is being increased, this will result in a volume of cornea above sphere 40' will be removed by ablation. In the process, the area containing the HIGH point 14 may be removed and a new HIGH point 14' is created. On the other hand, when the radius of curvature of the cornea is to be decreased, the above construction may result in a sphere 40 which is spaced above the corneal surface in some region about the HIGH point 14. It then becomes necessary to shift the center O of sphere 40' axially inward until the HIGH point 14 lies on the surface of sphere 40' or, preferably, to eliminate essentially all space between the corneal surface and the spherical surface, as explained below.

According to the invention, the entire surface of the cornea 18 that projects above the imaginary sphere 40' within the bounded region 16 is ablated. The surface to be ablated is determined by locating portions of the cornea that project above the sphere 40', for example, by integrating a region 44 of the cornea 18 above the continuous sphere 40' of radius R' across the bounded region 16. The region 44 defines the locations at which the sphere 40' intersects the cornea 18, and the coordinates of such locations that project beyond the sphere 40' are derived from the surface model of the cornea to drive a laser control system.

On the other hand, the determination of when to stop ablation is preferably based on having achieved a predetermined area (or volume) of space between the ablated cornea 18 and the sphere 40', which is preferably zero so that the ablated area of the cornea 18 becomes the shape of the sphere 40'. At this stage, these determinations are made on a programmed digital computer by surface or volume integration techniques, by a least squares technique, or otherwise, so as to minimize or zero the difference between the cornea 18 and the sphere 40' upon ablation of the corneal surface.

Ablation is performed so that the anterior surface portion 16a is ablated to a "smooth surface." Preferably, the "smooth surface" has zero space between the ablated cornea 18 and the sphere 40'. When this is achieved, the anterior surface portion 16a of the cornea 18 is coextensive with the spherical surface. This is achieved in a typical cornea by ablating about 5–8 $\mu$m of corneal material, although the degree of ablation required to smooth the cornea, that is, remove undulations, varies from patient to patient.

As a practical matter the formation of a spherical region on an ellipsoidal cornea must produce irregularities in the surface. For this reason, the spherical region S limited to less than the maximum available radius and a transition region T is provided from the spherical region out to the edge of the bounded region 16. For example, the FDA permits ablation out to a diameter of 6 mm. The preferred process of the invention therefore initially selects a spherical region which is 6 mm wide and a 1 mm wide skirt is provided as a transition region from the edge of the bounded region to the spherical surface.

In the preferred embodiment of the invention, a non-optimal transition region is constructed for simplicity. The transition region is constructed by generating a surface to fit a set of transition curves. Pairs of transition curves are constructed in a plane containing the corneal z axis, after which the plane is rotated by 50 and another pair of transition curves is generated, and so forth until the plane has been rotated to its starting position. Each time the plane is rotated, the intersection of the plane with the spherical surface defines a segment of a great circle. The transition curves are constructed at either end of that segment. To construct a transition curve, a straight line segment is initially generated between the point at which the plane intersects the periphery of the bounded region and a point on the great circle which is 1 mm away. The transition curve is derived by incrementing the z coordinate of the line segment by 10 m at its midpoint and constructing a circular arc which passes through this elevated point and terminates at the two end points of the line segment. Although the resulting set of transition curves does not produce an optimum transition surface, it provides satisfactory results.

It is contemplating that optimum smoothness of the post-operative cornea would be obtained by producing a transition region that matches the slope of the spherical region at one end and, at its other end, matches the slope of the corneal surface at the periphery of the bounded region. This could be achieved by a similar procedure to the one described above. Instead of circular arcs for the transition curves, one would construct: smooth curves that match the slope (first derivative) of the circular segment at one end of the line and, at the other end of the line, match the slope of the intersection between the plane and the corneal surface. Algorithms that achieve this are well-known and are used, for example, in performing filleting in drafting programs.

The selective ablation procedure can be performed with equal facility with respect to one or more rotationally offset arcs taken along the corneal surface. The arcs, as seen in FIG. 3, define a plurality of lines 5 on the anterior surface portion 16a which extend through the HIGH point 14 and substantially along the plane of a great circle. The "great circle," as previously noted, is defined by a plane containing the local z-axis 17.

One such arc 12 is shown in FIG. 3. Arc 12 has a line segment 12a extending from the peripheral point 34a to the HIGH point 14 and another line segment 12b that extends from a peripheral point 34b to the HIGH point 14. The path length of lines 12a, 12b in any given plane will typically differ, in the pre-operative eye, because of the particular topology of the cornea 18, which is usually aspheric and asymmetrical. See generally, for example, U.S. Pat. No. 5,502,518 issued Mar. 26, 1996 to Dr. David M. Lieberman for ASYMMETRIC ASPHERIC CONTACT LENS, for a discussion of the asphericity and asymmetry of the cornea, the disclosure of which is hereby incorporated by reference as if set forth fully herein.

Local high points along a particular one of the lines 12 are ablated using the laser in order to center the HIGH point 14 relative to line segments 12a, 12b in each plane. In particular, one or more local high points 46 on either side of the HIGH point 14 are ablated by controlling the locations of the bounded region 16 to which the laser applies energy. The result of these selective ablations is a more direct and shortened path from the HIGH point 14 to the periphery of the cornea 18 as compared to the unablated corneal surface.

The path lengths on either side of the HIGH point 14 are reevaluated after one or more of these ablations to determine whether further ablation is required to center the HIGH point 14 with respect to the line 12 being selectively ablated. If the HIGH point 14 is centered with respect to that one line 12 (at least to a predetermined acceptable degree, for example, one micron), then no more ablations are required in that plane. Otherwise, the highest local high point 46 that remains on the side of the HIGH point 14 with a longer path length is ablated by providing these coordinates to the laser.

Preferably, this procedure of selecting a line 12 in a plane that is perpendicular to the base plane BP, evaluating it for local high points 46, and directing a laser to ablate the local high points 46 until the HIGH point 14 coincides with the center of the ablated line is repeated with different lines 12 until the HIGH point 14 is equidistant from the periphery of the bounded region 16, as measured along the surface of the cornea. The number of lines 12 that should have their respective centers coincide with the HIGH point 14 affects the accuracy of the procedure. The more lines 12 that are evaluated and ablated, the greater the likelihood of achieving a post-surgery symmetrical cornea. Further, the coincidence of the HIGH point 14 and the center of any of these lines need only lie within a predefined degree of accuracy, for example, one micron, and need they not coincide exactly.

The foregoing procedure is preferably started by defining a plurality of lines 12 on the surface of the cornea 18, each in the plane of a great circle, and then selecting that line 12 which is least centered with respect to the HIGH point 14 for the ablation procedure. This least centered line 12 is then selectively ablated only at its highest points, as previously described, until the HIGH point 14 is equidistant from the periphery of the bounded region 16 within a predefined degree of accuracy. Additional lines 12 may then be selected subject to the criterion that they too be successively least centered with respect to the HIGH point 14, or perhaps based on other criteria, and then have their respective local high points 46 ablated. This process of selecting the least centered line 12 and ablating the local high points 46 may be repeated until the HIGH point 14 is equidistant from the periphery of the cornea 18 with respect to a preselected number of lines 12, within a predefined degree of accuracy.

As a modification of the foregoing, the first selected line 12 is that line 12 that is least centered, as previously described, and the following steps are repeated with respect to the next least centered line 12', after centering the least centered line 12 and so on, until the HIGH point 14 is equidistant within a predefined degree of accuracy: (a) the HIGH point 14 is identified, (b) a plurality of lines 12 are defined on the surface of the cornea substantially in the plane of a great circle, (c) only local high points 46 on the cornea which lie on one of the defined lines 12 are ablated by a laser to center the HIGH point 14 with respect to one of the defined lines 12.

Any undulations in the plane of the great circle of a selected line are smoothed by ablating the corneal material that projects above an arc that satisfies the following criteria: (1) the arc has its apex centered relative to the HIGH point 14; and (2) the arc passes through the bounded region 16 at peripheral locations 34 which are substantially 180° offset from the z-axis of the HIGH point 14.

Preferably, the radius of the arc along each selected line is the radius that just permits the arc to lie entirely below the corneal surface, and the greatest radius among these radii is preferably used to selectively ablate the cornea along all of the lines 12. The ablation is thus repeated with additional lines 12 until, for example, there is less than about a zero to four micron deviation, and preferably a zero micron deviation, between the spherical arc and each selected line at any location therealong, and repeated until a single radius describes the arc along each of the lines.

The aforementioned ablation procedure causes the optical center of the eye to align with the "HIGH point" of the cornea, which results in a spherical and symmetrical post-ablation cornea.

Uniform Corneal Ablation Using a Mask

In the event that a smoothing mask has been applied to the cornea 18, uniform ablation of the anterior surface portion 16a can be performed rather than the previously described selective ablation technique.

Figure 5:
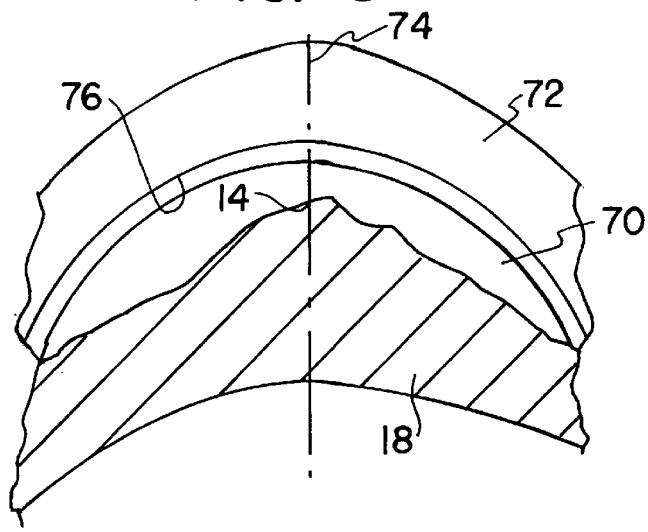
FIG. 5 is a schematic cross-sectional view of a cornea of an eye having a mask and shaping lens positioned thereupon.

Once the HIGH point 14 has been located, the optical center of the eye can be aligned with the HIGH point 14 by depositing a moldable mask 70 onto the cornea 18, and placing the posterior surface 76 of a lens 72 over the moldable mask 70 such that the optical center 74 of the lens 72 aligns with the HIGH point 14 (FIG. 5). The moldable mask 70 is thereby molded to the shape of the posterior surface 76 of the lens, which is preferably toric in shape in the region which overlies the anterior surface portion 16a.

A presently preferred material for the mask 70 is A Type 1 collagen. The collagen mask is heated to a temperature of about 42° C. to 45° C. so that it assumes a syrup-like viscosity. The heated collagen is deposited as a film on the cornea where it immediately begins to cool to body temperature (37° C.) at which temperature it assumes a gel-like consistency. Prior to cooling, the lens 72 is positioned on the collagen film so that the optical center 74 of the lens 72 aligns with the HIGH point 14, as illustrated in FIG. 5. Once the collagen gel has cooled and set, the positioned lens 72 will have molded the collagen into a spherical surface having its apex centered about the HIGH point 14. The lens 72 can then be discarded.

The cornea plus collagen gel have a smooth, undulation free surface. Uniform ablation of the masked anterior surface portion 16a can then proceed by ablating the masked cornea to a depth sufficient to remove all of the gel, in a manner known to those skilled in this art. Because the collagen and cornea ablate at the same rate (they are virtually identical materials, hence the preference for this material), uniform ablation will result in a smooth spherical corneal surface.

For reasons already explained, the collagen mask is preferably formed with a width of 6 nm, and a 1 mm skirt defines a transition region. This transition region may be formed in a separate step, after the contact lens is removed, or the posterior surface of the contact lens may be ground so as to have a smoothly curved transition lip.

Method and Apparatus for Radial Keratotomy

According to the invention, incisions are made on the cornea with regard to the surface topology of the cornea 18 in three-dimensional space to weaken the corneal walls and to permit the cornea to sit flat and symmetric with respect to the HIGH point 14. As in conventional procedures, a marker is used to delineate an outer region 60 within which the radial slices are made, as shown in FIG. 6. The outer region 60 has a circular two-space projection on the x- and y-axes extending, for example, up to about 1 to 3 mm from the periphery 34 of the cornea 18, and typically about 9 mm to 12 mm in diameter. On the other hand, an inner region 62 has an irregular (arbitrary) two-space projection because the radial slices b, b' are of equal length on the cornea 18, as described below.

The size of the outer region 60 and the relative size of the inner region 62 are selected based on a patient-by-patient basis with regard to the amount of correction required. The length of the radial slices directly affects the amount of weakening in the corneal walls and the tendency of the cornea 18 to collapse upon itself and, thereby, sit flatter. Accordingly, the amount of correction provided to a patient is directly related to the length of the radial slices that are made, which is in turn a function of the relative sizes of the inner and outer regions 62, 60, respectively. Nomographs have been compiled which describe the length of the incisions to be made in two-space for a prescribed working region and a given corneal sagittal depth. These lengths, however, do not reflect the true incision length on the surface of the cornea, which varies with sagittal depth and the asymmetry of the cornea in which the incisions are made. Accordingly, it is preferred that these lengths be modified (lengthened) based on empirical data gathered from procedures, which establishes a correlation between the two-space monographs and the true incisions lengths. A working region 64 between the inner and outer regions 62, 60 is where the radial incisions are made, and typically starts about 3–5 mm from the HIGH point 14 of the outer region 60 and extends to the periphery of the outer region 60 which is about 9 mm, and up to about 12 mm from the HIGH point 14.

The HIGH point is used as a reference point for a circular projection along the local z axis 17 of the cornea on the anterior surface of the cornea. The center of the inner region 62 typically differs from that of the outer region 60 (before the radial incisions are made) due to the variations in the corneal surface in the working region 64. However, both rejoins are made to align substantially with the HIGH point by forming a pair of incisions b, b' along the corneal surface. The incisions b, b' are preferably equal in length; however, the length of the respective incisions b, b' may be varied in a controlled manner to achieve a substantially spherical anterior surface portion 16a, which is the goal of the procedure. The boundary of the inner region 62 is determined by the encroachment of the incisions b-b' towards the HIGH point and varies across the surface of the cornea 18 due to the variations in the corneal topology.

Of course, if the inner region 62 is provided with a circular two-space projection along the z axis 17 of the cornea on the anterior surface of the cornea, then the outer region 60 would typically have an irregular shape, especially if the incisions b, b' are made the same length. In this case, the HIGH point for the donut-shaped working region 64 in which the incisions are to be made cannot be defined without first selecting the length of the radial slices along the cornea, which is done based on the surgeon's discretion and experience, or by a programmed computer after determining the degree and relative position of any asymmetry or asphericity on the corneal surface, and comparing the determined information to a knowledge base of a digital computer memory device. Once the lengths of each pair of the incisions has been selected, the incision lengths are added to the radius of the inner region 62 to define the peripheral points 34a', 34b' of the outer region 60 along the surface of the cornea.

As in conventional procedures, the radial incisions range from 4 to 16 in number (usually an even number of incisions), and are spaced apart by 90° down to 22½° depending on the number of cuts. In addition, arcuate incisions may be made to correct for pre-surgery astigmatism or to account for any surgically induced astigmatism.

As compared to prior art RK procedures in which the radial incisions are made with respect to the line-of-sight, the present procedure results in more a spherical and symmetrical post-RK cornea. Further, the present RK procedure causes the optical center of the eye to align with or more closely approximate the "HIGH point" of the cornea.

An improved apparatus for performing radial keratotomy is described next.

Figure 8:
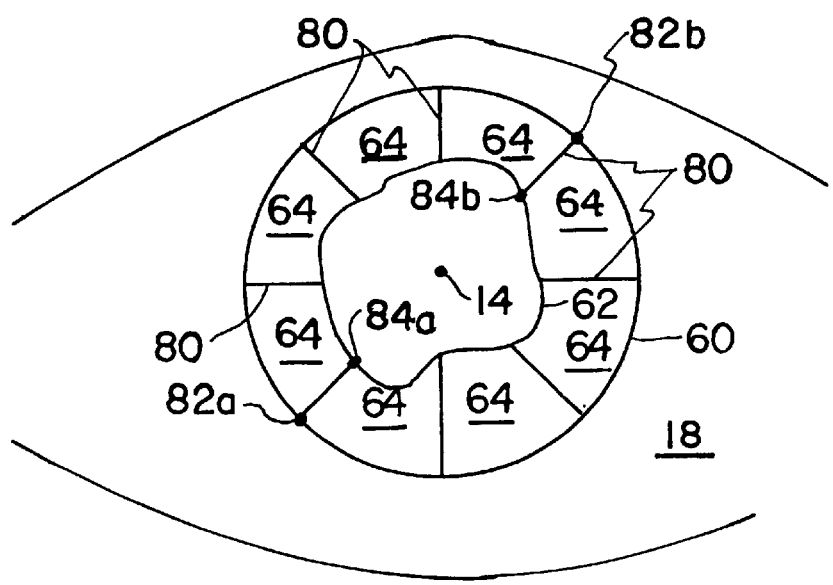
FIG. 8 is a schematic top view of the anterior corneal surface prior to performing a radial keratotomy procedure using an apparatus according to the invention.

The apparatus for performing radial keratotomy provides the surgeon at least with indicia of the outer and inner regions 60, 62 on the anterior surface of the cornea 18 to delimit the region 64 in which radial slices are to be made. As illustrated in FIG. 8, the apparatus further provides radial lines 80 on the corneal surface which extend, from opposing peripheral locations 82a, 82b toward the HIGH point 14 to guide the surgeon's hand in making the incisions b,b'. Eight radial lines 80 are illustrated, spaced 45° apart. The radial lines 80 have a length on the corneal surface such that incisions in the cornea 18 which are coextensive with the radial lines 80 will weaken the corneal walls. This causes the cornea 18 to bow outward at its sides so that the arc of the central portion of the cornea within the inner region 62 will be reduced and the cornea 18 will sit flatter, that is, have a reduced sagittal depth. As a result of making the incisions b,b' coextensive with the radial lines 80, the post-operative optical center more closely approximates the pre-operative HIGH point 14.

The apparatus includes a housing for a conventional RK cutting tool such as a diamond blade. The housing includes a suction port so that it can be fixed in position relative to the cornea using a vacuum device during the surgical procedure.

The cutting tool is mounted for rotatable and radial movement across the surface of the eye, and has a contact (down) position in which the cutting tool incises the cornea 18 and a standby (up) position in which the cutting tool is clear of the corneal surface. This is so that repositioning of the cutting tool can be achieved without cutting the cornea or disengaging the housing from the cornea. The housing is positioned on the cornea with regard to the indicia of the outer and inner regions 60, 62, for example, by aligning a circular suction mount on the forward end of the housing (that which engages the cornea 18) to the outer region 60. This assumes that the outer region 60 is circular; however, as noted above, the inner region 62 may be circular and the outer region 60 irregular.

Preferably, the indicia of the outer and inner regions 60, 62 are projected onto the anterior surface of the cornea 18 as a regular and an irregular shape, for example, by a collimated light beam. The regular shape, which can be either of the outer and inner regions 60, 62, alternatively may be placed on the cornea by a marker in conventional manner. The regular shape preferably has a circular two-space projection. However, the irregular shape must be determined with regard to the actual (three-dimensional) surface of the cornea. Accordingly, a programmed computer generates a surface model of the cornea so that the path lengths for the radial lines 80 can be determined. The radial lines have a predetermined length, as determined on a patient-by-patient basis with regard to printed or computer-readable nomographs, as previously described. The radial lines extend radially inward along the corneal surface toward the HIGH point 14 from a point on the periphery 82a to a point 84a which lies on the peripheral boundary 84 of the inner region 62. The peripheral boundary of the inner region 62 is determined with regard to the path lengths of a plurality of radial lines 80 along the surface of the cornea. The boundary of the irregular shape is determined with regard to the plurality of radial lines 80. The boundary of the irregular shape may be continuous or discontinuous. In any event, the first and second shapes are disposed on the anterior surface of the cornea such that one generally surrounds the other.

The irregular shape is preferably defined on opposite sides of the HIGH point 14 by equidistant path lengths along the anterior surface of the cornea and in the plane of a great circle so that the cornea sits flat. As previously noted, the actual path lengths are determined on a patient-by-patient basis. Because the cutting tool is rotatably mounted, radial incisions can be made in the plane of one or more great circles.

The cutting tool can be programmed to make the cuts along the projected lines 80 using position sensors for sensing the current position of the cutting tool, and light or heat sensors to detect the locations of the lines 80. In a fully automated system, the lines 80 need not be projected onto the cornea 18. Rather, a programmed computer can determine the location and extent of the incisions required to cause the optical center of the eye to align or more closely approximate the "HIGH point" of the cornea.

Non-Surgical Treatment

Figure 9:
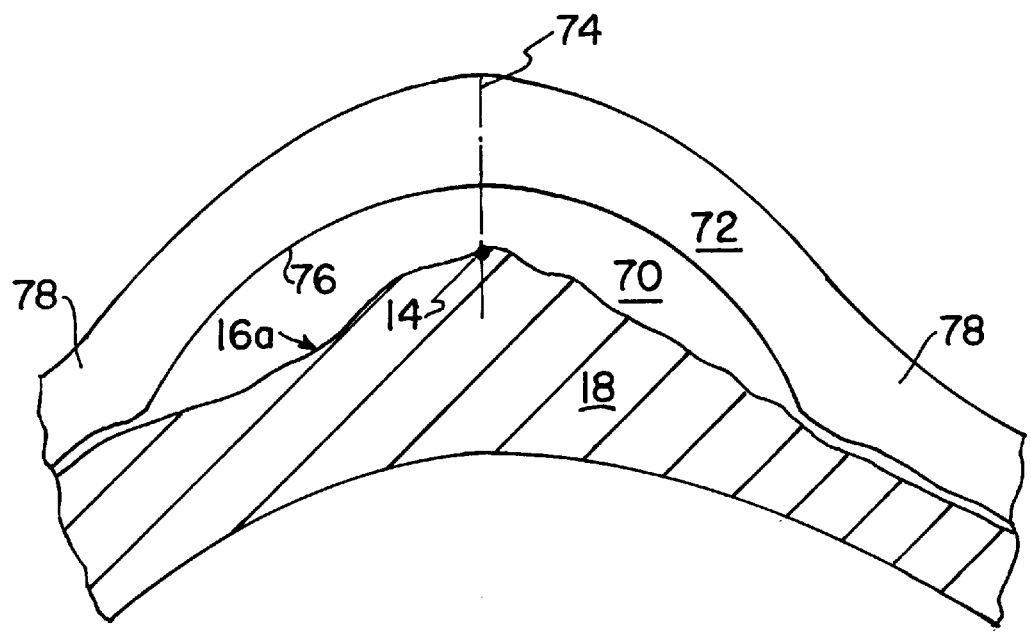
FIG. 9 is a schematic cross-sectional view of a cornea of an eye illustrating the non-surgical treatment of the eye to align the optical center with the geometric center, by making use of a special contact lens, which is self-orienting to achieve that result.

As mentioned previously, the present invention also contemplates the non-surgical treatment of the eye by utilizing a contact lens to align the post-treatment optical center with the HIGH point of the cornea. The process makes use of a lens which orients itself into a known physical position when placed in the eye of the patient. Such a lens is disclosed in the aforementioned copending U.S. Pat. No. 5,502,518 issued Sep. 9, 1993, for ASYMMETRIC ASPHERIC CONTACT LENS. In accordance with that patent, a peripheral region 78 of a contact lens 72 is conformed closely to the surface topology of the patient's cornea. When such a lens 72 is placed in the patient's eye, it will orient itself so the topologically matched portions are in engagement. In accordance with the present invention, such a lens 72 is constructed so that its optical center 74 will overlie the HIGH point of the anterior surface portion 16a of the cornea when the lens positions itself over the eye. Preferably, the lens 72 is a toric lens having a major optical axis and a minor optical axis arranged relative to the eye, once positioned, so that the patient looks through the optical center 74 of the lens. Referring to FIG. 9, it will be appreciated that, when such a lens 72 is placed over the eye, it will orient itself so that the optical center 74 of the lens 72 overlies the HIGH point 14. The central portion of the lens would be shaped to achieve the desired correction of vision in the same manner as any other contact lens.

Method for Diagnosing and Analyzing the Human Eye

It has been found that the cornea modelling methods which are described below are particularly effective in diagnosing and analyzing an eye. Specifically, the methods are useful in determining whether a particular clinical technique would be appropriate for a particular patient's eye, in planning the actual procedure, and in predicting the likely results of that procedure.

Presented below are actual computer-generated models of the eye of a real patient. For purposes of demonstration, models will illustrate the results obtained when performing corneal ablation on the patient's eye to achieve a four diopter visual correction utilizing different points and different ablation waxes. In the process, the superiority of the ablation method of the present invention is demonstrated.

Figure 10A:
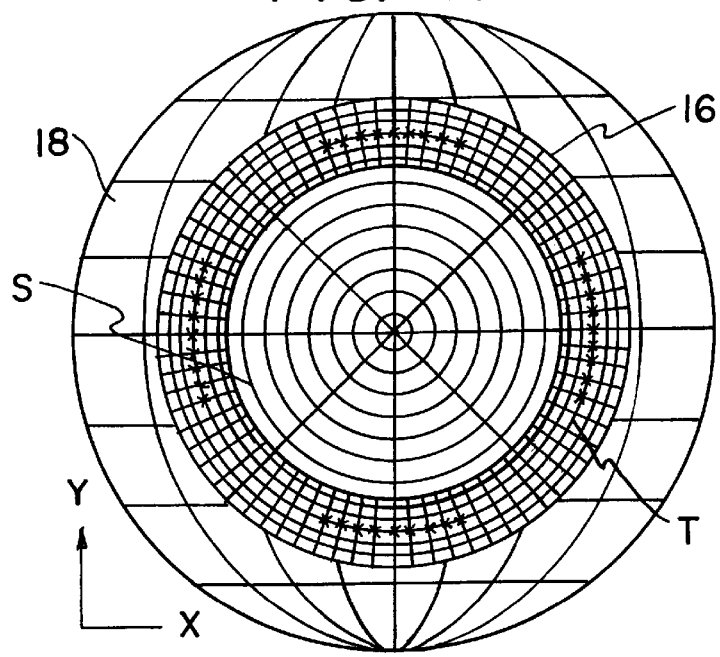
FIGS. 10A, 10B, 10C and 10D, is a printout of various views of a computer-generated model (produced in accordance with the present invention) of a post-operative cornea on which laser ablation surgery has been performed about the pupillary axis.
Figure 10B:
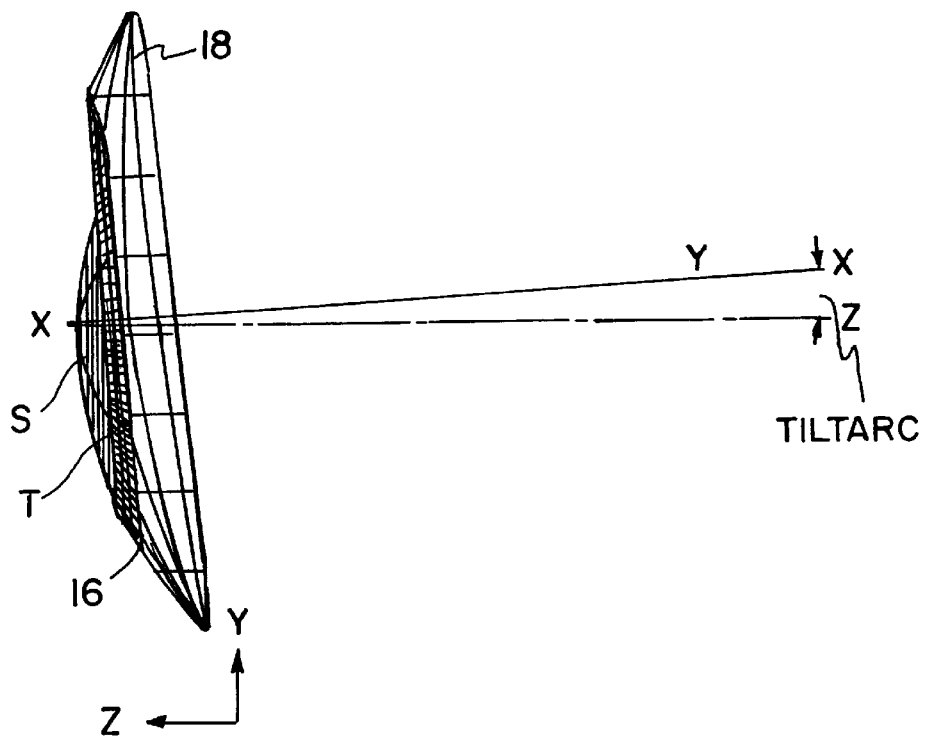
Figure 10D:
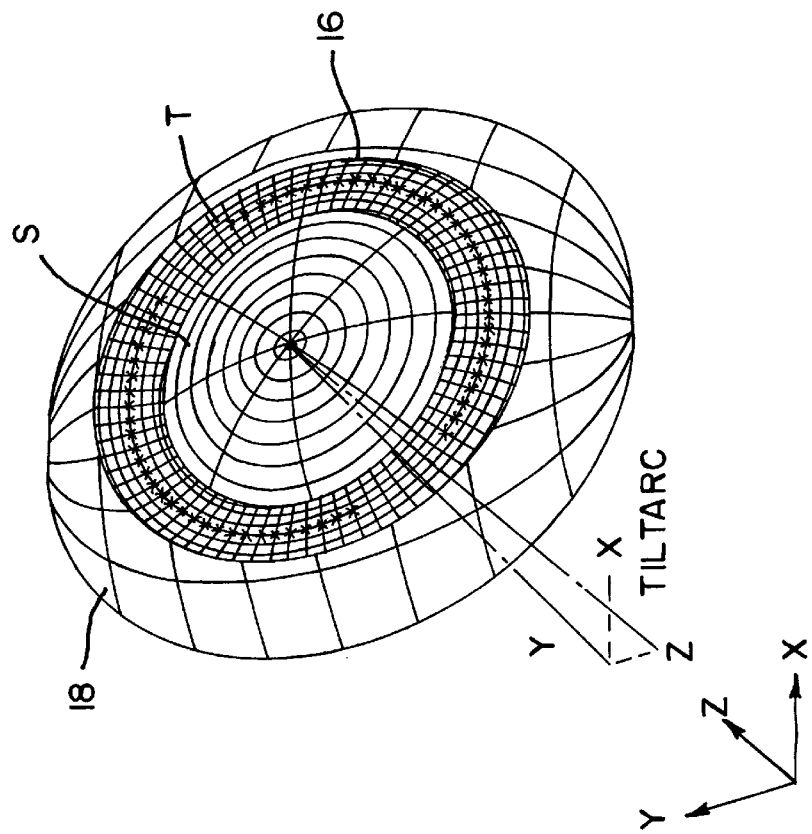
Figure 10C:
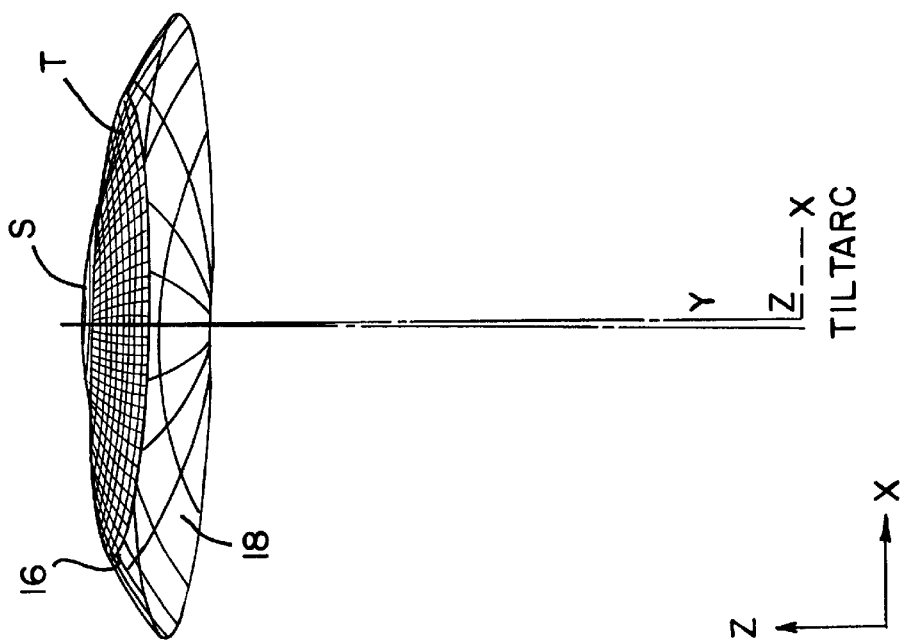
Figure 11A:
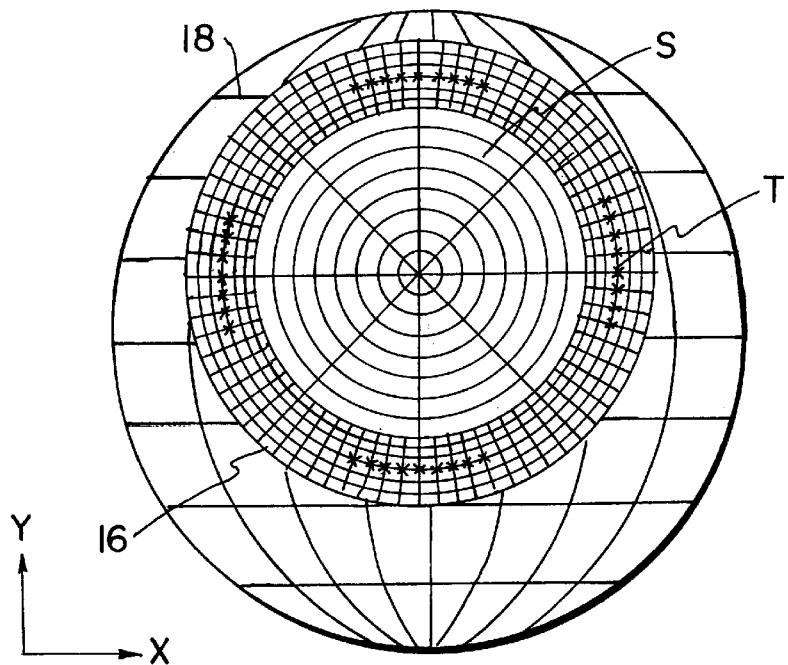
FIGS. 11A, 11B, 11C and 11D, is a printout similar to FIG. 10 showing the same eye after corneal ablation about a tilted axis passing through the HIGH point.
Figure 11B:
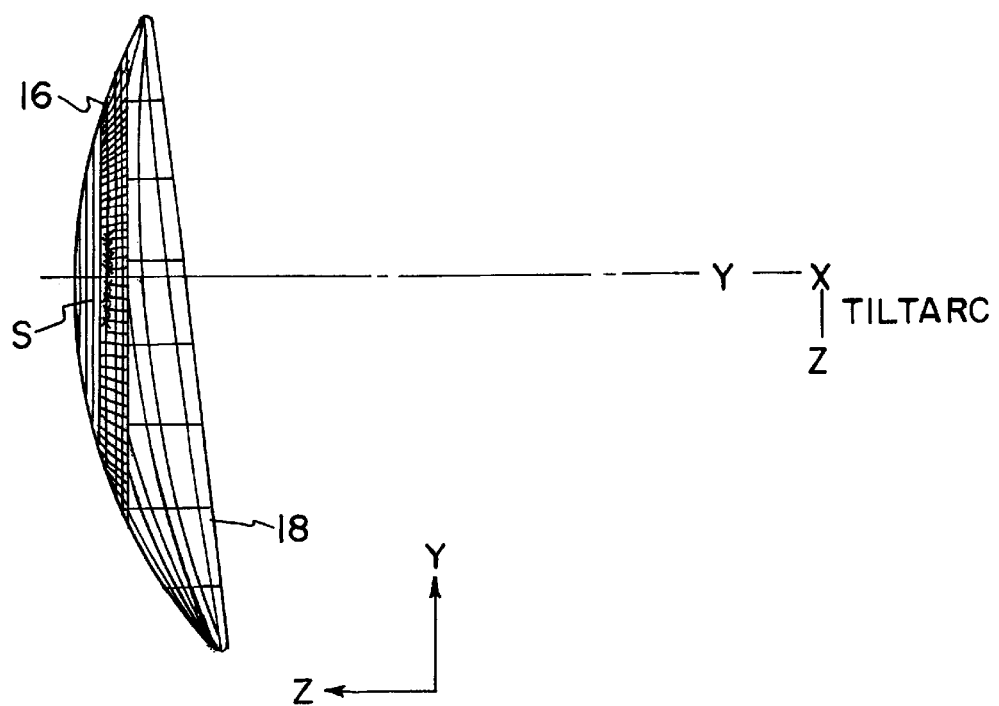
Figure 11D:
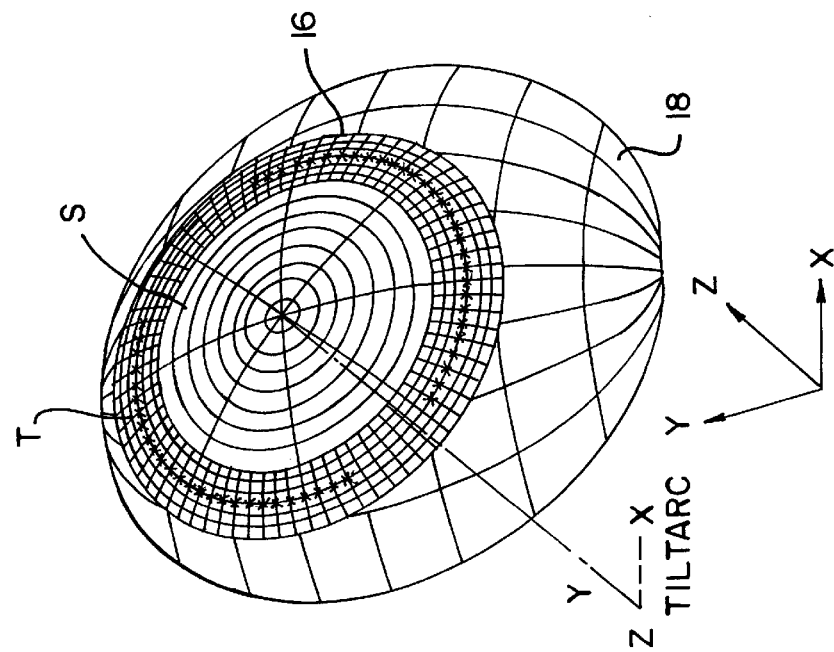
Figure 11C:
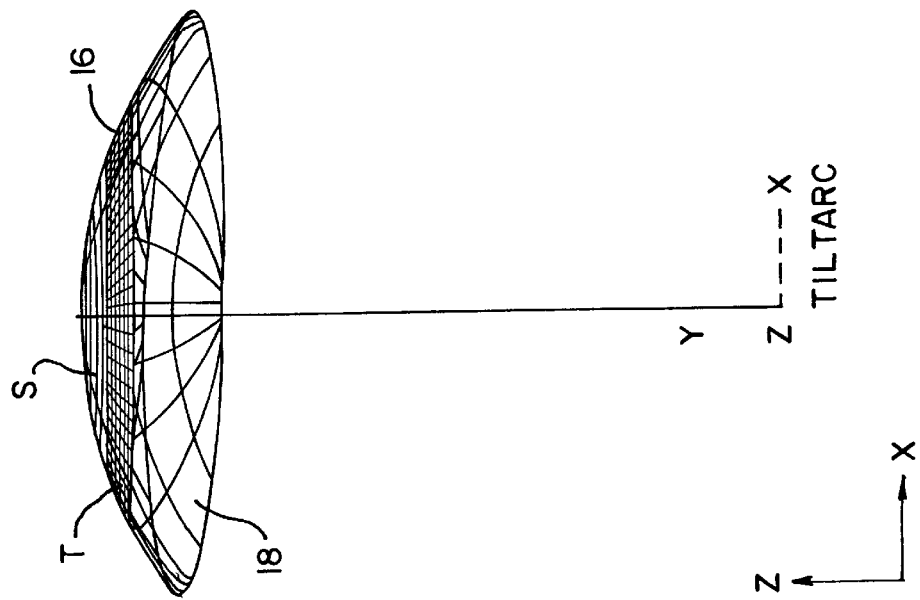

FIGS. 10A–D are front, top, side and perspective views, respectively, generated by the modeling, method of the present invention and demonstrating the effect of performing corneal ablation surgery utilizing the pupillary axis as a reference axis. Ablation was performed within a 3 mm radius about the pupillary axis by providing a spherical surface out to a 2 mm radius and introducing a 1 mm wide skirt as a transition region between the spherical surface and the cornea 18. In the postoperative eye, the bounded region 16 of the cornea is therefore made up of a spherical region S which is designed as if it extended out to a width of 6 mm, but a transition region or skirt T is provided so as to extend between the ellipsoidal surface of the cornea and the spherical surface. As a convention, the z-axis is defined to extend from the reference plane towards the front of the cornea. As best seen in FIG. 10B, the bounded region 16 exhibits a substantial forward tilt relative to the y-axis (6.9°) and a slight rightward tilt of 1.3° relative thereto (see FIG. 10C). However, since in the example of FIG. 10 ablation occurred about the pupillary axis, no account was taken of the cornea tilt, as is common in ablation procedures currently performed.

Such, ablation performed in this manner tends to over-ablate some areas (e.g. the top portion of bounded region 16 in FIG. 10B) and to under ablate others (e.g. the bottom portion of bounded region 16 in FIG. 10B). It is should also be observed that the upper portion of bounded region 16 in FIG. 10B is quite, irregular. This is, in fact, the result that would be obtained by the current conventional technique of ablating about the pupillary axis.

In order to arrive at this result, it was initially determined that the best fit spherical surface 40 on the pre-operative cornea was a 6 mm wide section of a sphere having a radius of 5.87 mm. Examination of the patient revealed that the eye required a four diopter correction, which the result that the post-operative spherical region S is required to have a radius of curvature of 7.19 mm. This was the actual radius to which the spherical region S was ablated in the model.

If the present analysis were performed pre-operatively, the surgeon would most likely conclude that the results of this operation would be unsatisfactory and that this patient was not a good candidate for this operation, owing to the nature of the pre-operative cornea and the degree of correction required.

FIG. 11, comprising FIGS. 11A–11D, contains the same views as FIG. 10, but illustrates the results of performing ablation operation on the same eye, but using a tilted axis through the HIGH point as a reference axis. As was the case in FIG. 10, the spherical region is formed as if it had a diameter of 6 mm, with a transition skirt T being provided. When centered about the HIGH point, the bounded region exhibits a tilt of only 0.178° in FIG. 11B and a tilt of 0.27° in FIG. 11C. The pre-operative best fit spherical region S was determined to be a 6 mm wide section of a sphere having a radius of 7.36 mm. In order to obtain a 4 diopter correction, this radius was increased to 8.08 mm, at which radius ablation was performed on the model to remove all portions of the bounded region that protruded above the sphere with that diameter positioned so as to remove all space between the sphere and the corneal surface. It will be appreciated from FIG. 11, the post-operative cornea will be quite smooth and will exhibit no irregularities.

In performing corneal ablation surgery, it is desirable to remove the least amount of corneal material possible. The Anvil 5000 program which was utilized to create the surface models in accordance with the present invention (see the immediately following subsection) has a provision for measuring the included volume under a specified area. Utilizing this feature, the volume included under the pre-operative cornea was measured to be 46.0 cu.mm. After the operation of FIG. 10, the volume was 35.4 cu.mm, while after the operation of FIG. 11, the 39.4 cu.mm bounded region 16 was measured in FIGS. 10 and 11. The substantially greater included volume in FIG. 11 demonstrates that the procedure of FIG. 10 removed more material than was necessary.

This discussion has demonstrated the value of the modelling techniques of the present invention as a diagnostic tool in planning and evaluating corneal procedures. Prior to the present invention, a practitioner might well have undertaken an operation of the type demonstrated in FIG. 10, only to discover after the fact that it was of little, if any, benefit. Worst yet, it is conceivable that such a procedure could introduce vision problems that are worse than the ones being corrected.

Generation of the Surface Model

The preferred embodiment makes use of a topological modeling software product available under the name "Anvil 5000" from Manufacturing Consulting Services of Scottsdale, Ariz. This computer program permits programming of complex geometric procedures and complex surface modelling through the use of the GRAPL language.

With further reference to step 24 of FIG. 1, a surface model is generated by arranging the CTM data into subsets of ordered triples, each of the subsets defining the knot points for a spline over an interval defined by the subset. The spline fits the CTM data to a curve having continuous first and second derivatives at the knot points (referred to herein as a "smooth curve"). Typically, the knot points in the CTM data are equidistant in the x- and y-directions due to the manner of operation of conventional corneal topographic scanning devices, which have a resolution that varies from about forty to two-hundred microns.

The arrangement of the subsets of ordered triples is arbitrary, but should bear a logical relationship to the Cartesian CTM data. The subsets of ordered triples are arranged, for example, in rows or columns with respect to the Cartesian coordinates of the CTM data, or in radial lines emanating from a particular coordinate in the CTM data, for example, the coordinate having the greatest z-coordinate value (the HIGH point), is located by a conventional sorting routine. More than one subset of ordered triples may be contained in a given row, column, or radial line if a further partitioning of the data is desired.

As should be readily appreciated, at least three knot points are required to form a spline. Additional knot points over the same interval increase the accuracy of the resulting spline; however, there is a concomitant sacrifice of computational speed to process this additional data. Preferably, twenty-six or more knot points define the splines used to form the surface model when CTM data having a 200 micron resolution is used. The surgeon must strike a balance between accuracy and speed, especially when the surgery is being performed in realtime with the acquisition of the CTM data. The speed of the system or method is affected by the number of knot points chosen and the choice of computer, e.g., one having sufficient memory and perhaps a math co-processor.

Each subset of ordered triples forms a series of stored data points, represents a portion of the CTM data, and defines a different set of discrete knot points that are applied to a spline equation to generate a smooth curve ("spline"). When the subsets are arranged in rows or columns, all of the CTM data is represented. When the subsets are radially arranged, a substantial portion of the CTM data is represented. About fifty to sixty subsets of ordered triples are formed when a corneal topographic scanning device having a resolution of about 200 microns is used to generate a surface model from the unprocessed CTM data. This is because the cornea has about 10 to 12 $mm^2$ of surface to be scanned. Preferably, the subsets are arranged relative to one another so that the entirety of the CTM data is utilized in step 24, for example, in rows or columns.

Preferably, a nonuniform-rational Basis ("NURB") equation is used to generate a so-called "B-spline," although other less preferred spline equations can be used such as a uniform-rational basis, cubic, or bezier spline. The choice of spline equation is guided by the regularity, variation, range, and spacing of the data, as understood by those skilled in the art. See, e.g., Rogers and Adams, MATHEMATICAL ELEMENTS FOR COMPUTER GRAPHICS, p. 446 (2d. Ed.). Splines interpolate the points beyond the resolution of the unprocessed CTM data, and thereby provide information beyond the point-to-point behavior of the CTM data between the points in the subset. Certain information is derived from the spline, including tangent, normal, and cross products (more generally referred to herein as "vectorial products") which provides surface behavior information between the subsets.

It is preferred that the surface model of the cornea be derived from the CTM data by applying to a surface equation both the data that is used to generate the splines (namely, the subsets of ordered triples used to generate the splines) and the data that is derived from the splines (the vectorial products). The preferred surface equation for use with the NURB equation is a NURB-surface equation. The NURB-surface equation fits a closed, finite set of points between the splines. See Rogers and Adams, MATHEMATICAL ELEMENTS FOR COMPUTER GRAPHICS, ch. 6, pp. 379–479. The surface model generated from the NURB-surface equation defines a smooth, free-form surface. The Cartesian coordinates of the surface model represent an averaging and smoothing of the unprocessed CTM data, as well as a smoothing of the splines used to generate the surface. As a result, coordinates on the surface model typically differ from the CTM data and the splines, yet provide an accurate representation of the cornea.

The surface model is displayable on a computer's monitor so that the surgeon can assess whether there are areas on the patient's cornea to avoid, either because of a prior surgery or insufficient or aberrant CTM data. A bounded region 16 in which work is to be performed for a surgical procedure on the cornea is defined by the surgeon or a programmed computer, as described above. The bounded region 16 encompasses the relevant portion of the surface model for steps 26 through 30 of FIG. 1.

APPENDIX OF DEFINITIONS

The foregoing terms are assigned the meanings described below.

(a) Knot points, or ordered triples, are the x-, y-, z-coordinates that define the raw data provided from a corneal topographic scanning device.

(b) A point cloud is a unique universe of all the x-, y-, z-coordinates within a given bounded area. The bounded area typically includes all the knot points that are incorporated into a surface model, as defined below.

(c) A spline equation is a mathematical tool for generating a smooth curve containing a discrete set of selected knot points. The smooth curve is called a "spline," and a spline of order K is defined as a piecewise polynomial function of order K on some (finite or infinite) interval with K-2 continuous derivatives there. See, e.g., de Boor, A PRACTICAL GUIDE To SPLINES, p. 125 (Springer Verlag).

(d) Spline points are interpolated points along the spline.

(e) Vectorial products are derived from the spline and may include a tangent vectorial product (first derivative), a normal vectorial product (second derivative), cross products, other order derivatives, and twist vectors. The vectorial products are directional in a relative sense, that is, there is a sign ("+" or "−") associated with the difference between adjacent knot points, and the sign imparts direction information that is useful in establishing convergence to the HIGH point, as described above.

(f) A surface equation uses the discreet sets of knot points that generate the splines and the vectorial products derived from the splines to generate a free-form surface.

(g) A free-form surface is one which is not spherical, cylindrical, or any other predictable Euclidean shape, for example, the anterior surface of the edge.

(h) A surface model is a three-dimensional free-form surface defined by the surface equation. Because the surface model is fitted to both the knot points in the point cloud and the vectorial products of a group of splines, coordinates on the surface model along the z-axis will differ somewhat from those of the knot points and the splines.

Having thus described a preferred embodiment of the present invention, it is to be understood that the above described device and method is merely illustrative of the principles of the present invention, and that other devices may be devised by those skilled in the art without departing from the spirit and scope of the invention as claimed below.

What is claimed is:

1. A method for diagnosing and analyzing the cornea of an eye, said method being performed with the aid of a computer system including a graphic display device, said method comprising the steps of:

running a topological modeling computer program on said computer system;

reading into said computer system data representing sampled points on a corneal topography map of the surface of the cornea of the eye, said map being of the type produced by a corneal topography scanning machine;

utilizing said data in said computer program, to produce a surface model of at least a complete working area of said cornea which closely represents the surface of the cornea in three dimensions as a smooth, free-form surface such that any portion of the surface on said surface model can be manipulated in said computer system in the same manner as an actual surface; and displaying at least a portion of said surface model on said graphic display device.

2. The method of claim 1 further comprising processing said surface model to derive a parameter of the cornea.

3. The method claim 2 wherein said processing step comprises performing a measurement on said surface model to derive physical measurements of the cornea.

4. The method of claim 3 wherein said processing step comprises effecting a physical change thereto to simulate a physical change to the cornea.

5. The method of claim 4 wherein said physical change comprises forming cuts in the surface model to simulate corneal surgery.

6. The method of claim 4 wherein said physical change comprises removing a portion of the surface model.

7. The method of claim 1 wherein said producing step includes forming spline curves by utilizing a plurality of said sampled points for each curve, and utilizing a plurality of the spline curves to form a surface closely estimating the surface topology of the cornea.

8. The method of claim 7 wherein points are represented in the surface model which are beyond the resolution of the sampled points, providing information beyond the point-to-point behavior of the sampled points.

9. The method of claim 1 wherein points are represented in the surface model which are beyond the resolution of the sampled points, providing information beyond the point-to-point behavior of the sampled points.

10. The method of claim 9 further comprising processing said surface model to derive a parameter of the cornea.

11. The method claim 10 wherein said processing step comprises performing a measurement on said surface model to derive physical measurements of the cornea.

12. The method of claim 9 further comprising processing said surface model to effect a physical change thereto simulating a physical change to the cornea.

13. The method of claim 12 wherein said physical change comprises forming a cut on the surface model, to simulate corneal surgery.

14. A method for diagnosing and analyzing the cornea of an eye, said method being performed with the aid of a computer system including a graphic display device, said method comprising the steps of:

running a topological modeling computer program on said computer system;

reading into said computer system data representing sampled points on a corneal topography map of the surface of the cornea of the eye, said map being of the type produced by a corneal topography scanning machine, in which the coordinates of all sampled points are relative to a reference plane;

utilizing said data in said computer program, to produce a surface model of at least a complete working area of said cornea which closely represents the surface of the cornea in three dimensions as a smooth, free-form surface such that any portion of the surface on said surface model can be manipulated in said computer system in the same manner as an actual surface, said model having a perimeter lying substantially in a base plane which intersects the reference plane of sampled points; and displaying at least a portion of said surface model on said graphic display device.

15. The method of claim 14 further comprising effecting a physical change to the model to simulate a physical change to the cornea.

16. The method of claim 15 wherein said physical change comprises one of cutting and removing a portion of the model surface to simulate corneal surgery, the cutting and removing being performed with reference to a tilted axis which is substantially perpendicular to the base plane.

17. The method of claim 16 wherein the cutting and removing are performed with reference to a point defined by the intersection of the tilted axis and the surface of the model.

18. The method of claim 17 wherein the tilted axis passes through that point on the surface of the model which is most distant from the reference axis.

* * * * *